United States Patent
Kondo

(10) Patent No.: US 9,526,464 B2
(45) Date of Patent: Dec. 27, 2016

(54) RADIATION IMAGING APPARATUS

(71) Applicant: CANON KABUSHIKI KAISHA, Tokyo (JP)

(72) Inventor: Hiroto Kondo, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 14/198,311

(22) Filed: Mar. 5, 2014

(65) Prior Publication Data

US 2014/0252229 A1    Sep. 11, 2014

(30) Foreign Application Priority Data

Mar. 6, 2013   (JP) ................................ 2013-044508

(51) Int. Cl.
   *G01T 7/00*    (2006.01)
   *A61B 6/00*    (2006.01)
   *G03B 42/04*   (2006.01)

(52) U.S. Cl.
   CPC .............. *A61B 6/4283* (2013.01); *A61B 6/44* (2013.01); *A61B 6/4233* (2013.01); *A61B 6/56* (2013.01); *G03B 42/04* (2013.01)

(58) Field of Classification Search
   CPC ..................................... G01T 7/00; G01T 1/24
   USPC ....................................................... 250/336.1
   See application file for complete search history.

(56) References Cited

U.S. PATENT DOCUMENTS

| | | | | |
|---|---|---|---|---|
| 6,278,120 B1* | 8/2001 | May | | 250/372 |
| 7,330,526 B2* | 2/2008 | Singh | | 376/272 |
| 7,482,595 B1* | 1/2009 | Ertel | | 250/370.09 |
| 8,526,196 B2* | 9/2013 | Eichner et al. | | 361/807 |
| 2004/0234040 A1* | 11/2004 | Okamura et al. | | 378/199 |
| 2006/0138340 A1* | 6/2006 | Ianakiev et al. | | 250/390.01 |
| 2008/0095324 A1* | 4/2008 | Watanabe | | 378/198 |
| 2010/0304213 A1* | 12/2010 | Breimon et al. | | 429/185 |
| 2012/0069966 A1* | 3/2012 | Kobayashi | | 378/189 |

FOREIGN PATENT DOCUMENTS

| | | |
|---|---|---|
| JP | 2002-311527 A | 10/2002 |
| JP | 2012-63326 A | 3/2012 |

* cited by examiner

*Primary Examiner* — Marcus Taningco
(74) *Attorney, Agent, or Firm* — Canon USA Inc., IP Division

(57) ABSTRACT

A radiation imaging apparatus includes a casing having an opening at a portion other than a radiation receiving surface thereof, a cover member attached to the opening, and a first seal member for effecting sealing between the interior of the radiation imaging apparatus and the opening arranged at the peripheral edge portion of the opening. By attaching the cover member, the hermeticity of the radiation imaging apparatus due to the first seal member is improved.

13 Claims, 6 Drawing Sheets

RADIATION IMAGING APPARATUS

BACKGROUND

Field

Aspects of the present invention generally relate to a radiation imaging apparatus equipped with a radiation detection unit configured to detect radiation transmitted through a subject and to convert this radiation into an electric signal, and having an opening at a part of its casing.

Description of the Related Art

With the recent progress in semiconductor processing technology, a digital radiography (DR) apparatus configured to take a radiation image using a semiconductor sensor has come to be widely used in the medical field. As compared with a conventional radiation photography system employing a photosensitive film, this system exhibits a very wide dynamic range, and is advantageous from the practical point of view in that it can obtain a radiation image not affected by fluctuations in radiation exposure amount.

Use of this apparatus is expected in every conceivable case in and out of hospitals. Since satisfactory portability and operability are required of this apparatus, a reduction in size, thickness, and weight of the apparatus is in progress. In addition, taking the general versatility of the apparatus into consideration, the thickness of the apparatus is required to be restrained to approximately 15 mm so that the apparatus can be inserted into a Bucky's unit used in a conventional film cassette. From the viewpoint of improving the portability and operability of the radiation imaging apparatus, the cable for supplying power to the imaging apparatus is very inconvenient. Further, there is a fear that a person may be caught by an extra cable and fall down, or may damage the imaging apparatus and the control unit. Further, in a clean (sterilized) environment such as an operation room, the imaging apparatus inclusive of the cable is prohibited to come into contact with an un-sterilized area such as the floor surface. To solve the above problems, a wireless type DR apparatus has come to be widely used.

In the wireless type DR apparatus, a power supply source for supplying power to the apparatus is indispensable. Some DR apparatuses have a built-in power supply source, which is not detachable. DR apparatuses, however, in which the power supply source is detachable have also come to be widely used. In this detachable type apparatus, an opening is provided at a part of the casing thereof, and a member for storing a battery is mounted to that opening (See Japanese Patent Application Laid-Open No. 2012-63326). According to Japanese Patent Application Laid-Open No. 2002-311527, a cover is provided at the opening, thus taking airtight property into consideration. There exist a lot of wired type apparatuses each having a power cable, each of which is provided with an access cover for the replacement of the cable and the replacement of the electric board.

The above-described radiation imaging apparatuses are often used in direct contact with a patient in every possible condition, so that, after the use, the radiation imaging apparatus is subjected to cleaning, disinfection, sterilization, and the like without fail. At that time, in order to effect the above-mentioned disinfection and sterilization, there is frequently used, instead of water, an organic solvent or a liquid containing a sterilizer.

A DR apparatus contains a lot of electric boards, and if liquid enters the DR apparatus, failure or ignition of these electric boards may occur. In particular, in a case of a DR apparatus having an access cover, a gap may be formed between the access cover and the casing exterior, and, in a case of a DR apparatus having a detachable battery, a gap may be formed between the battery and the battery storage portion, or between the battery storage portion and the casing exterior, which leads to an increase in the risk of intrusion of the above-mentioned liquid. When the opening is exposed at the time of replacement of the battery or for temporary maintenance of the imaging apparatus, there is a fear that liquid will easily enter the interior of the imaging apparatus.

Further, in such a structure, there is also a fear of leakage of light through the above-mentioned gap. As is generally known, the radiation light receiving portion (sensor portion) of a DR apparatus is deteriorated by light. To fill the gap, the parts are glued to each other by adhesive, or the parts are given pressure, for example, by fastening them together by screws with a seal member or the like being held therebetween. In the former case, when a trouble such as damage of either of the parts glued together occurs, an increase in the cost due to the replacement of the part is involved, resulting in an unsatisfactory maintainability. In the latter case, the casing exterior and an inner component of the DR apparatus are fastened together, so that, when the DR apparatus is dropped down, all the weight of the apparatus interior must be supported by the fastening screws. Therefore, the screws and the portion around the fastened portions may be easily damaged. If, fearing this, the fastening by the screws were eliminated, a repulsive force striving to compress the seal member to a desired thickness may be increased, and the portion around the opening may be swollen. The solvent or the like exhibits a much lower surface tension than water, and more easily enters the gap. Thus, if the seal member is not compressed to the desired thickness, there is a fear that the liquid may enter the interior of the imaging apparatus.

SUMMARY

Aspects of the present invention are generally directed to a DR imaging apparatus having an opening at a part of a casing thereof capable of preventing failure of the apparatus due to intrusion of liquid or the like through the opening and deterioration in a sensor portion due to leakage of light.

According to an aspect of the present invention, a radiation imaging apparatus includes a radiation detection unit configured to convert radiation transmitted through a subject to an electric signal, a casing having an opening at a portion other than a radiation receiving surface of the radiation detection unit and configured to store the radiation detection unit, a cover member attached to the opening, and a first seal member arranged at a peripheral edge portion of the opening and configured to effect sealing between interior of the apparatus and the opening, wherein hermeticity of the radiation imaging apparatus due to the first seal member is improved by attaching the cover member.

Further features of the present disclosure will become apparent from the following description of exemplary embodiments with reference to the attached drawings.

DESCRIPTION OF THE EMBODIMENTS

Various exemplary embodiments, features, and aspects will be described in detail below with reference to the drawings.

Figure 1A:
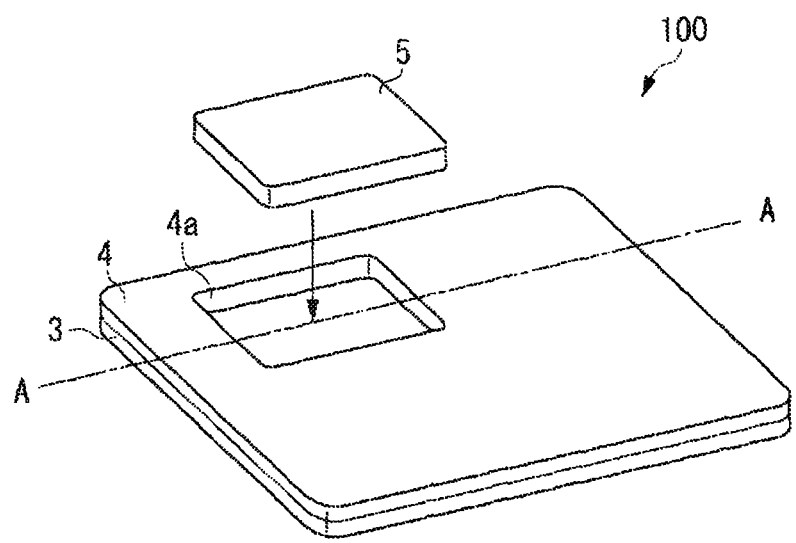
FIGS. 1A and 1B are diagrams illustrating a radiation imaging apparatus having an opening in a rear casing thereof according to a first exemplary embodiment.
Figure 1B:
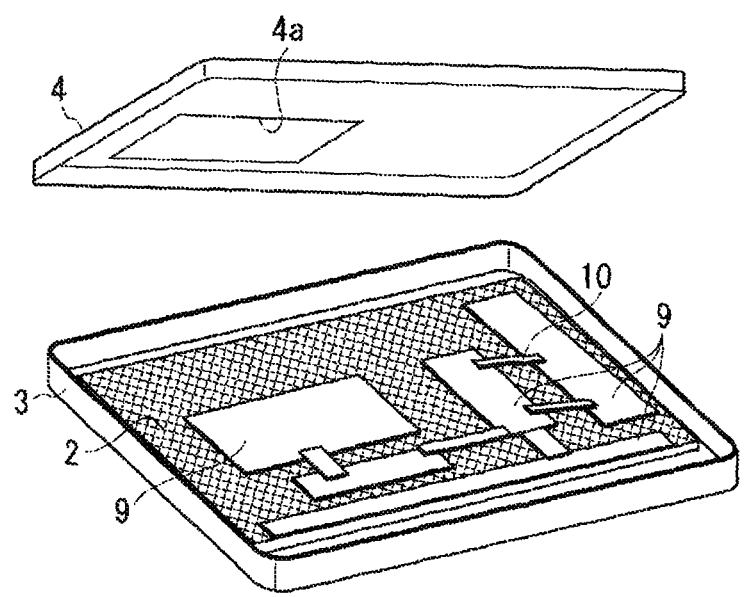
Figure 2:
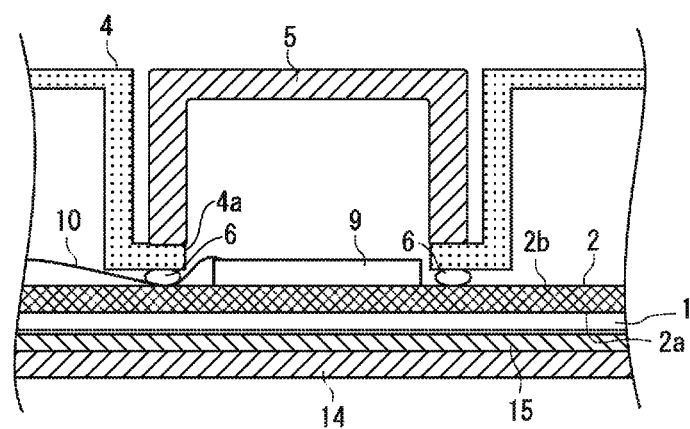
FIG. 2 is a partial cross-section diagram of the radiation imaging apparatus illustrated in FIGS. 1A and 1B.

FIGS. 1A and 1B are diagrams illustrating a principal construction according to a first exemplary embodiment. FIG. 2 is a sectional view taken along the line A-A illustrated in FIG. 1A. A radiation imaging apparatus 100 is formed by laminating fluorescent members configured to receive radiation transmitted through a subject and to convert the radiation to light, and has a radiation detection unit 1 (hereinafter referred to as the sensor) configured to convert the light to an electric signal. The sensor 1 is attached to a sensor retaining plate 2. As the material of the fluorescent members laminated to form the sensor 1, there is generally employed GOS ($Gd_2O_2S$) or CsI. Electric boards 9 are mounted on a surface 2b (opposite surface) of the sensor retaining plate opposite to a sensor attachment surface 2a, and the electric signal obtained through conversion at the sensor 1 is processed to generate image data. The generated captured image is transmitted by communication to an external display system (not illustrated), and is displayed. The communication method may be of either a wired type or a wireless type. In the case of a wireless type, a band of 2.54 GHz or 5 GHz is mainly used.

The exterior of the radiation imaging apparatus 100 is composed of a front casing 3 on the radiation reception side, a rear casing 4 having an opening 4a at a part thereof other than the radiation reception surface, and a cover member 5 filling the opening 4a. The opening 4a can be utilized for access to the electric boards 9 inside the radiation imaging apparatus 100. In the case where the radiation imaging apparatus 100 is of a wireless type, the opening can be utilized as a space for storing a battery, a portable terminal or the like. The opening 4a means a hole formed in the rear casing 4 in order to enable what has been mentioned above. The radiation reception side of the front casing 3 is substantially entirely open, and a radiation transmission plate 14 is attached t thereto, so that the sensor 1 can detect radiation transmitted through the subject. Further, the radiation transmission plate 14 also functions as a support member configured to receive a weight from the subject. The front casing 3 and the rear casing 4 are formed of aluminum alloy, magnesium alloy or the like, which is of lightweight and high rigidity. By being covered with such casing, the sensor 1 is protected.

The electric boards 9 are mounted on the surface 2b of the sensor retaining plate 2 opposite to the sensor attachment surface 2a, and process the radiation received by the sensor 1 to convert it into image data. The image obtained through the conversion is transferred to a personal computer (PC), a tablet or the like in a wireless or a wired manner to be confirmed. The electric boards 9 are mutually connected by a flexible cable 10. Further, as illustrated in FIG. 2, a protective sheet 15 is laid between the sensor 1 and the radiation transmission plate 14.

As illustrated in FIG. 2, the opening 4a has a three-dimensional configuration, and a seal member 6 (first seal member) is arranged at an inner peripheral edge portion of the opening 4a. The seal member 6 is arranged so as to contact the sensor retaining plate 2 in the configuration of the opening 4a of the rear casing 4, whereby the seal member can be compressed (pressurized) between the above two components. As a result, even in a state where no cover member is mounted, it is possible to prevent leakage of light and intrusion of water into the interior of the radiation imaging apparatus 100 via the opening 4a, by the sealing effect of the seal member 6. While an elastic member formed of an elastic material such as silicone rubber or foam is desirable for the seal member 6. However, it is not limited thereto, and the seal member may also be made of an adhesive member. When an elastic member is used, the member must be compressed by a certain amount to prevent intrusion of water. In a case of a rubber O-ring generally used, a crushing amount of approximately 8 to 30% may be required. The above compression causes generation of a repulsive force, and due to this repulsive force, the gap is shielded, and a sealing effect is exerted. Further, from the viewpoint of sealing property, it is advantageous that not only the compressive force exerted on the seal member but also the contact area of the member held in contact with the seal member should be as large as possible. In the construction of the present exemplary embodiment, the opening 4a of the rear casing 4 and the portion in the vicinity thereof are not fastened or bonded to other members such as the sensor retaining plate 2. Thus, there is no regulation in thickness in the direction in which the seal member 6 is compressed, and there is a fear that the portion around the opening 4a will be swollen due to the above-mentioned repulsive force and that both the compressive force and the contact area will be reduced to be smaller than the desired values. When, due to the restriction in thickness of the imaging unit, the seal member crushing amount in design is approximately 8% of that mentioned above, there is the possibility that this value cannot be attained. Here, the cover member 5 is further mounted to the radiation imaging apparatus 100 while being held in contact with a part of the opening 4a, whereby the opening 4a is pushed-in, the compressive force and the contact area with respect to the seal member 6 is increased, and the swelling of the opening 4a and the portion in the vicinity thereof can be suppressed. By thus increasing and improving the hermetic-sealing force due to the seal member 6, it is possible to prevent intrusion of water due to high hydraulic pressure, and intrusion of chemicals, solvent or the like the surface tension of which is lower than that of water into the interior of the radiation imaging apparatus 100. In terms of waterproof standard according to Japanese Industrial Standards (JIS), it is possible to increase the IPxx level by mounting the cover member 5.

With this construction, when a seal member is also arranged between the cover member 5 and, for example, the opening 4a, it is possible to prevent intrusion of liquid not only from the opening 4a into the interior of the radiation imaging apparatus 100 but also from the exterior of the imaging unit into the interior of the cover member 5. The seal member is arranged at the peripheral edge portion of the cover member 5, or at the base peripheral edge portion of the cover member 5 which is bent into a box-like configuration.

Figure 3A:
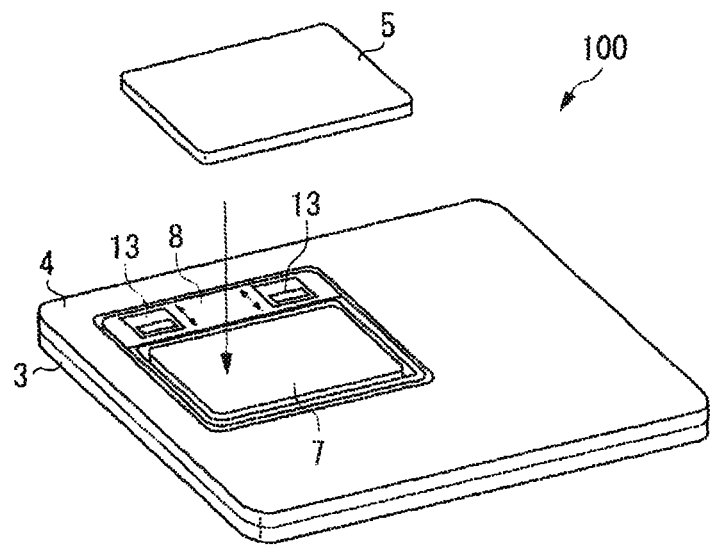
FIGS. 3A and 3B are diagrams illustrating a radiation imaging apparatus having an opening for attaching and detaching a battery according to a second exemplary embodiment.
Figure 3B:
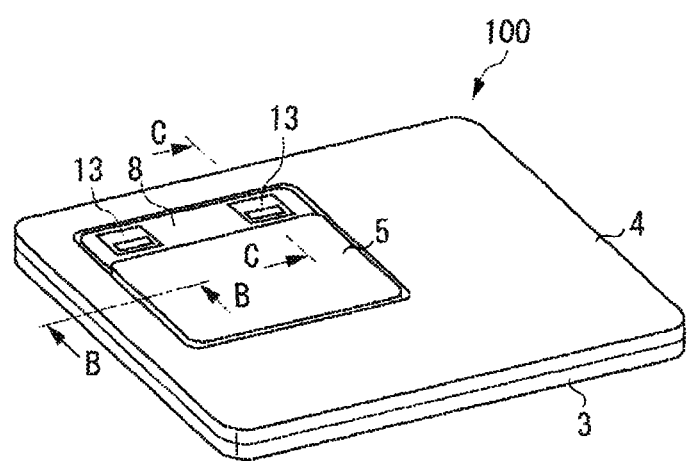
Figure 4:
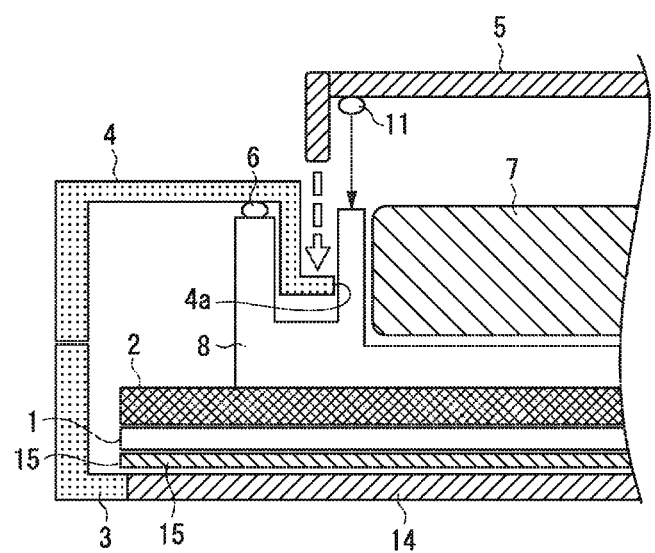
FIG. 4 is a partial sectional view, taken along the line B-B, of the radiation imaging apparatus illustrated in FIGS. 3A and 3B.

FIGS. 3A and 3B illustrate a wireless type radiation imaging apparatus 100 with a battery mounted therein for driving the radiation imaging apparatus 100 according to a second exemplary embodiment. FIG. 4 is a sectional view taken along the line B-B illustrated in FIG. 3B. The members that are the same as or correspond to those of the first exemplary embodiment are designated by the same reference numerals. A detachable battery 7 is mounted on the radiation imaging apparatus 100 as the power supply source, and the battery 7 is inserted into a battery holder 8 mounted on the sensor retaining plate 2, i.e., the battery holder 8 can accommodate the battery 7. The battery holder 8 is formed in a shape to be fit-engaged with the opening 4*a* provided in the rear casing 4, and is arranged at a corresponding position. While a lithium ion battery is generally used as the battery 7, it is not limited thereto.

As in the case of the first exemplary embodiment, the peripheral edge portion of the opening 4*a* is formed in a Z-shaped sectional configuration (FIG. 4), and the seal member 6 is arranged in the outer periphery of the peripheral edge portion (on the sensor side of the rear casing 4), and is compressed between the peripheral edge portion and the battery holder 8. By fastening the front casing 3 and the rear casing 4 together, the seal member 6 is compressed, and light leakage and water intrusion via the gap between the opening 4*a* of the rear casing 4 and the battery holder 8 can be prevented. The battery 7 inserted into the battery holder 8 serving as the storage portion of the battery 7 is connected to a connector (not illustrated) attached to the battery holder 8 to supply electric power to the radiation imaging apparatus 100.

Further, a cover member 5 to which inner peripheral edge portion a second seal member 11 is attached is fitted into the battery holder 8 accommodated in the opening 4*a* so as to cover the battery 7. FIG. 3B illustrates a state where the cover member 5 is attached to the radiation imaging apparatus 100. The peripheral edge portion of the opening 4*a* of the rear casing 4 is of a Z-shaped configuration, so that when the cover member 5 is fitted into the battery holder 8, the cover member 5 comes into contact with the Z-shaped portion of the opening 4*a*, and thereby the seal member 6 (as in the first exemplary embodiment) is compressed. Further, the second seal member 11 comes into contact with the battery holder 8, and is compressed between the cover member 5 and the battery holder 8. In this connection, it is desirable for the two seal members 6 and 11 to be formed of the same material as the seal member 6 according to the first exemplary embodiment so that they can cope with the repeated compression, the warpage of the members held in contact therewith, and their surface undulation. By attaching the cover member 5 having the second seal member 11, the opening 4*a* of the radiation imaging apparatus 100 can have a further hermetic structure. Further, when a packing member such as an O-ring is also arranged at the fit-engaged surfaces of the front casing 3 and the rear casing 4, the radiation imaging apparatus 100 as a whole can have a hermetic structure. Fastening by screws is adopted for the mating of the front casing 3 and the rear casing 4, whereby it is possible for the packing member arranged to attain a desired crushing amount.

Figure 5:
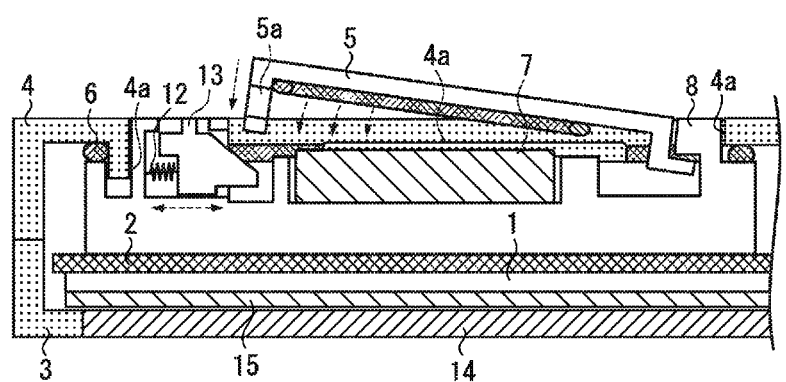
FIG. 5 is a partial sectional view, taken along the line C-C, of the radiation imaging apparatus illustrated in FIGS. 3A and 3B.

As illustrated in FIG. 5, the cover member 5 is fixed by inserting a lock 13 of the battery holder 8 into a hole 5*a* of the cover member 5. There is provided at least one lock 13 at the inner region of the battery holder 8. In the example illustrated in FIGS. 3A and 3B, there are provided a pair of locks 13. The locks 13 are arranged in the space between the seal member 6 and the second seal member 11, whereby there is no need to machine a hole for the operation of the locks 13 in the cover member 5. Thus the hermetic structure of the radiation imaging apparatus 100 can be easily maintained. It is desirable to arrange a plurality of locks 13. By enabling them to slide independently, it is possible to prevent the locks 13 from being inadvertently released, and to reduce the risk of fall of the cover member 5 and the battery 7. The direction of sliding of the locks 13 is not limited to the direction of the arrow in FIG. 5 but can be set as appropriate.

In the present exemplary embodiment, the battery 7 and the cover member 5 are formed as separate objects, it is also possible to integrally form them, or to form the battery 7 itself to have the function of the cover member 5 through its shape. In this case, the same effect can be attained by arranging the second seal member 11 at the peripheral edge portion.

Figure 6:
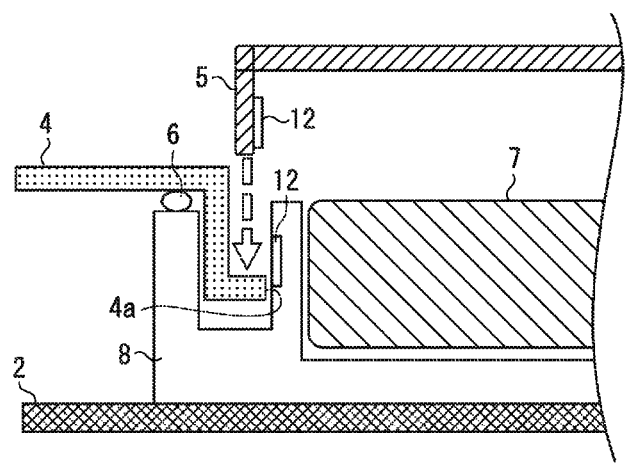
FIG. 6 is a diagram illustrating a radiation imaging apparatus according to a third exemplary embodiment.

FIG. 6 is a diagram illustrating how a detection sensor 12 is provided on the radiation imaging apparatus 100 and on the cover member 5. As described according to a first exemplary embodiment and the second exemplary embodiment, the radiation imaging apparatus 100 can be realized in a hermetic structure by attaching the cover member 5. In this case, at the time of using the radiation imaging apparatus 100, the effect of the hermetic structure cannot be achieved if the cover member 5 is not attached. By installing the detection sensor 12 on the cover member 5 and on the portion in the vicinity of the mounting position of the cover member 5 inside the imaging apparatus 100, it is possible to detect whether the cover member 5 has been attached or not.

In the case where the cover member 5 is not attached in the normal way, a sequence of prohibiting the power source of the radiation imaging apparatus 100 from turning on, i.e., not allowing operation may be employed, whereby it is possible to maintain the state in which the radiation imaging apparatus 100 can always be used in a hermetic structure. The detection sensor 12 can be appropriately selected from among a high-frequency oscillation type sensor, a magnetic type sensor, an electrical capacitance sensor, a light detection type sensor, etc. In the present exemplary embodiment, the sensor is mounted separately on both the radiation type imaging apparatus 100 and the cover member 5, it is also possible to employ a detection sensor of the type to be solely mounted on one of them.

Further, to detect the condition of the locks 13 for fixing the cover member 5, it is also possible to mount on the locks 13 a detection sensor for detecting the lock condition. In this case, by detecting the movement amount of the locks 13 by the detection sensor, it is possible to grasp the fixed or released (or detached) state of the cover member 5, and the stability or instability of the fixing condition can be grasped. By employing a sequence not allowing the power source to be turned on when the locks 13 are not at the normal cover fixing positions, it is possible to avoid an unstable fixing condition.

As described above according to the first exemplary embodiment and the second exemplary embodiment, when the seal member 6 and the second seal member 11 are formed as elastic members, a repulsive force is generated at the time of compression. The cover member 5 is attached so as to be in contact with the Z-shaped portion of the opening of the rear casing 4, whereby the repulsive force is directly received. One side of the cover member 5 is fixed to the rear casing 4 by a hinge unit. Alternatively, a claw-like member is formed so as to be detachable through rotation in a cantilever-like fashion. Due to the mechanism allowing attachment and detachment through rotation, the cover member 5 is caused to pop up by the elastic force of the seal member, and thus the attachment and detachment can be easily performed. When the seal member is not formed of an elastic member, the cover member 5 exhibits no pop-up function. Therefore, it is important for the seal member to be an elastic member. For the cover member 5 to pop up, it is only necessary to form at least the seal member 6 as an elastic member, and the material of the seal member 11 is not limited.

According to the exemplary embodiments, in a radiation imaging apparatus having an opening at a part of the casing thereof, even when a cover of the opening is detached, it is possible to secure the sealing force and to prevent intrusion of light and water, and when the cover is mounted, the sealing force is further enhanced to prevent intrusion of liquid such as solvent into the interior of the apparatus.

While the present disclosure has been described with reference to exemplary embodiments, it is to be understood that these embodiments are not seen to be limiting. The scope of the following claims is to be accorded the broadest interpretation so as to encompass all such modifications and equivalent structures and functions.

This application claims the benefit of Japanese Patent Application No. 2013-044508, filed Mar. 6, 2013, which is hereby incorporated by reference herein in its entirety.

What is claimed is:

1. A radiation imaging apparatus comprising:
a radiation detection unit configured to convert radiation transmitted through a subject to an electric signal;
a casing having an opening at a portion other than a radiation receiving surface of the radiation detection unit and configured to store the radiation detection unit;
a cover member attached to the opening;
a holder capable of storing a detachable battery and arranged at the opening;
a first seal member arranged between a peripheral edge portion of the opening and the holder, and configured to effect sealing between interior of the apparatus and the opening; and
a second seal member arranged between the cover member and the holder, and configured to effect sealing between the interior of the cover member and the opening,
wherein hermeticity of the radiation imaging apparatus due to the first seal member and the second seal member is improved by pressing by the cover member.

2. The radiation imaging apparatus according to claim 1, wherein the radiation imaging apparatus and the holder for the battery are hermetically closed by respectively contacting the first seal member and the second seal member to the holder.

3. The radiation imaging apparatus according to claim 2, wherein the holder has at least one lock unit for fixing the cover member, and
wherein the lock unit is arranged in a space on an inner side of the opening and between the first seal member and the second seal member.

4. The radiation imaging apparatus according to claim 3, wherein radiation imaging apparatus has a plurality of lock units capable of independently sliding.

5. The radiation imaging apparatus according to claim 3, wherein the first seal member and the second seal member have a pop-up function by which the cover member is raised when the lock unit is released.

6. The radiation imaging apparatus according to claim 1, wherein at least the first seal member is an elastic member.

7. The radiation imaging apparatus according to claim 1, further comprising a detection sensor configured to detect attachment and detachment of the cover member, wherein, when it is detected that the cover member has been detached, or that the cover member has not been attached in a normal state, the radiation imaging apparatus is configured not to operate.

8. The radiation imaging apparatus according to claim 1, wherein the first seal member is an adhesive member and the second seal member is an elastic member.

9. A radiation imaging apparatus comprising:
a radiation detection unit configured to convert radiation transmitted through a subject to an electric signal;
a casing having a recessed portion configured to accommodate the radiation detection unit;
a battery holder arranged at the recessed portion and configured to store a battery;
a cover member detachably fixed to the battery holder;
a first member arranged between the recessed portion and the battery holder, and configured to isolate the casing's interior from the casing's exterior; and
a second member arranged between the battery holder and the cover member, and configured to isolate the interior of the cover member from the casing's exterior while receiving pressure from the cover member.

10. The radiation imaging apparatus according to claim 9, wherein the first member is an adhesive member and the second member is an elastic member.

11. The radiation imaging apparatus according to claim 9, wherein the cover member and the battery are integrally formed.

12. The radiation imaging apparatus according to claim 9, wherein the second member is fixed to the cover member.

13. A radiation imaging apparatus comprising:
a radiation detection unit configured to convert radiation transmitted through a subject to an electric signal;
a casing having an opening and configured to store the radiation detection unit;
a battery holder arranged at the opening;
a battery unit detachably fixed to the battery holder and including a cover member and a battery;
a first member arranged at between a peripheral edge portion of the opening and the battery holder, and configured to isolate the casing's interior from the casing's exterior; and
a second member arranged between the battery holder and the battery unit, and configured to isolate the casing's interior from the casing's exterior while receiving pressure from the battery unit.

* * * * *